United States Patent [19]

Murakami et al.

[11] 3,985,758
[45] Oct. 12, 1976

[54] 1,4-DIHYDROPYRIDINE DERIVATIVES
[75] Inventors: Masuo Murakami; Kozo Takahashi, both of Tokyo; Masaru Iwanami, Yokohama; Masaharu Fujimoto, Tokyo; Tadao Shibanuma, Asaka; Ryutaro Kawai, Shiraoka; Toichi Takenaka, Tokyo, all of Japan
[73] Assignee: Yamanouchi Pharmaceutical Co., Ltd., Tokyo, Japan
[22] Filed: June 6, 1975
[21] Appl. No.: 584,268

Related U.S. Application Data
[63] Continuation-in-part of Ser. No. 442,781, Feb. 15, 1974, abandoned.

[30] Foreign Application Priority Data
Mar. 3, 1973  Japan................. 48-25566
May 11, 1973  Japan................. 48-52307
July 24, 1973  Japan................. 48-83276
Nov. 29, 1973  Japan................. 48-134070
Feb. 20, 1973  Japan................. 48-20423
Apr. 20, 1973  Japan................. 48-44821

[52] U.S. Cl. .................... 260/295.5 R; 424/266
[51] Int. Cl.² ........................... C07D 213/55
[58] Field of Search ..................... 260/295.5 R

[56] References Cited
UNITED STATES PATENTS
3,905,970  9/1975  Bossert et al............ 260/247.2 B

*Primary Examiner*—Alan L. Rotman
*Attorney, Agent, or Firm*—Burgess Ryan and Wayne

[57] ABSTRACT

There are provided novel 1,4-dihydropyridine derivatives, particularly 2,6-dimethyl-4-(3'-nitrophenyl)-1,4-dihydropyridine-3,5-dicarboxylic acid 3-$\beta$-(N-benzyl-N-methylamino)ethyl ester and 5-methyl ester. The 1,4-dihydropyridine derivatives are characterized by cerebral vascular dilator activity.

9 Claims, No Drawings

1,4-DIHYDROPYRIDINE DERIVATIVES

This application is a continuation-in-part of U.S. Pat. Application Ser. No. 442,781, filed Feb. 15, 1974 and now abandoned.

BACKGROUND OF THE INVENTION

1. Field of the Invention

The present invention relates generally to novel 1,4-dihydropyridine derivatives and more particularly, it relates to the 2,6-di-lower alkyl-4-substituted phenyl-1,4-dihydropyridine-3-carboxylic acid aminoalkyl ester derivatives represented by the general formula

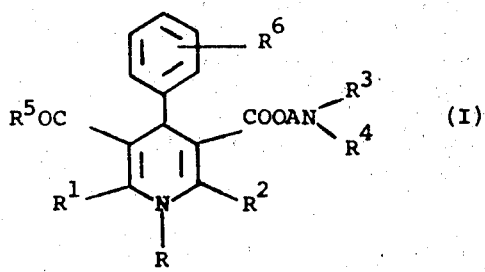

wherein R represents a hydrogen atom or a lower alkyl group; $R^1$ and $R^2$, which may be the same or different, each represents a lower alkyl group; $R^3$ represents a phenyl group, a phenyl lower alkyl group, a phenyl lower alkyl group substituted with a halogen atom, a lower alkyl group or a lower alkoxy group, $R^4$ represents a hydrogen atom or a lower alkyl group; A represents a lower alkylene group; $R^5$ represents a lower alkyl group, a lower alkoxy group, or a lower alkoxy group substituted with a lower alkoxy group or

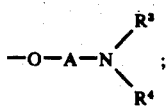

and $R^6$ represents a nitro group or a trifluoromethyl group.

The compounds of this invention have excellent cerebral vascular dilator activity.

2. Description of the Prior Art

As 1,4-dihydropyridine-3,5-dicarboxylic acid derivatives, 4-nitrophenyl-2,6-dimethyl-1,4-dihydropyridine-3,5-dicarboxylic acid dialkyl esters have been known from old as described in, for example, Chem. Ber. 20, 1338–1343 (1887) [4-(2',3' or 4'-nitrophenyl)-2,6-dimethyl-1,4-dihydropyridine-3,5-dicarboxylic acid diethyl ester] and J. Am. Chem. Soc., 71, 4003–4007 (1949) [4-(3'-nitrophenyl)-2,6-dimethyl-1,4-dihydropyridine-3,5-dicarboxylic acid dimethyl, diethyl or di-n-butyl ester].

And it is known that 4-(2'-nitrophenyl)-2,6-dimethyl-1,4-dihydropyridine-3,5-dicarboxylic acid dimethyl ester shows coronary vasodilator activity (U.S. Pat. No. 3,644,627).

Further, the compounds having pyridyl or pyrimidyl group instead of nitrophenyl at 4-position in the above-mentioned compounds have been also prepared (U.S. Pat. No. 3,470,297 or U.S. Pat. No. 3,511,837). However, free compounds of these compounds are poorly water-soluble and when these compounds are dissolved in water in the form of their salts, they are unstable (cf. U.S. Pat. No. 3,488,359 col. 2, lines 26–30).

Though it is described in U.S. Pat. No. 3,488,359 that hydroxyalkyl ester or alkoxyalkyl ester are soluble and stable in water either in the free form or in the form of their salts (col. 2, lines 22–25), practical example showing the excellent water-solubility of these esters is not described in the specification (especially, it is not described that the compounds are soluble in water at PH ranges wherein injection can be prepared).

Some other similar types of compounds are known [U.S. Pat. No. 3,511,837 (4-pyrimidyl-1,4-dihydropyridine derivatives) U.S. Pat. No. 3,691,177 (Cyanophenyl-1,4-dihydropyridine derivatives), German Offenlegungsschrift No. 1,813,436 (N-alkyl-1,4-dihydropyridine derivatives), No. 1,923,990 (N-alkyl-1,4-dihydropyridine derivatives), No. 1,963,185 (4-nitro and other group substituted phenyl-1,4-dihydropyridine derivatives), No. 1,963,186 (Sulfur containing 4-aryl-1,4-dihydropyridine derivatives), No. 2,005,116 (1,4-dihydropyridine-3,5-dicarboxylic acid unsaturated alkyl esters), No. 2,003,146 (3-alkanoyl-1,4-dihydropyridine-5-carboxylic acid esters)].

As a result of researching a series of these compounds, it was published in Naturwissenschaften 58, (11)578(1971) that 4-(2'-nitrophenyl)-2,6-dimethyl-1,4-dihydropyridine-3,5-dicarboxylic acid dimethyl ester) generic name: Nifedipine) shows much excellent coronary vasodilator activity and spasmolytic activity.

Further, it is known that 1,4-dihydro-2,6-dimethyl-4-(2'-trifluoromethylphenyl)-3,5-pyridine dicarboxylic acid diethyl ester shows hypotensive activity (U.S. Pat. No. 3,511,837). However, this compound is very poorly water-soluble [J. Pharm. Sci., 61, (10) 1686(1972)].

SUMMARY OF THE INVENTION

This invention is characterized first in that the ester part of the carboxylic acid ester is aminoalkyl ester, of which amino group is substituted by phenyl or aralkyl and secondly in that the compounds of this invention can form water-soluble mineral acid salt, different from a series of prior art. In addition, the compounds of this invention have cerebral vascular dilator activity and high water-solubility (which action and water-solubility is not known in the known compounds of prior art) and shows low toxicity.

That is, the inventors have discovered that the compounds represented by general formula (I)

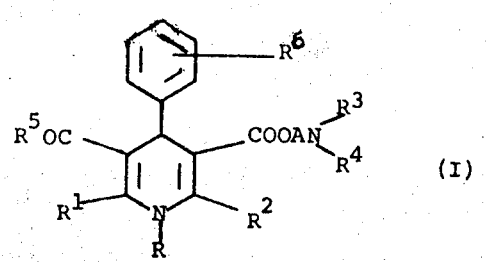

wherein R represents a hydrogen atom or a lower alkyl group; $R^1$ and $R^2$, which may be the same or different, each represents a lower alkyl group; $R^3$ represents a phenyl group which may have a substituent or an aralkyl group which may have a substituent; $R^4$ represents a hydrogen atom or a lower alkyl group; A represents a lower alkylene group; $R^5$ represents a lower alkyl group, a lower alkoxy group which may have been substituted by a lower alkoxy group;

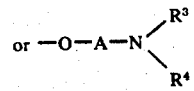

group; and $R^6$ represents a nitro group or a trifluoromethyl group; has musculotropic spasmolytic activity as well as particularly excellent cerebral vascular dilator activity and show low toxicity. Therefore, the compounds of this invention are particularly suitable for curing the obstruction of cerebral vascular blood flow.

Further, the salts of the compounds of this invention re suitable for liquid pharmaceutical preparation (especially injection), as the compounds of this invention are highly soluble in water.

Furthermore, the nitrogen-containing group-substituted alkyl esters of 1,4-dihydropyridine-3,5-dicarboxylic acid of this invention are not known and thus, quite unexpectedly, such novel compounds have the activities as described above.

DETAILED DESCRIPTION OF THE INVENTION

Now, the compounds of this invention represented by the general formula (1) are prepared by the following methods:

A. The benzaldenyde derivative represented by the formula II

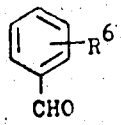   II wherein $R^6$ has the same significance as in general formula I, the lower alkanoylacetic acid aminoalkyl ester represented by the formula III

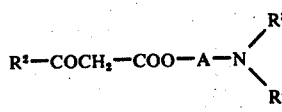   III wherein $R^2$, $R^3$, $R^4$, and A have the same significance as in general formula I, and the enamine derivative represented by general formula IV

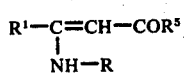   IV wherein R, $R^1$ and $R^5$ have the same significance as in general formula I are reacted in a substantially equimolar ratio without a solvent or in a solvent such as ethanol, isopropanol, dioxane, dimethylformamide, dimethyl sulfoxide, acetonitrile, etc. The reaction is promoted by heating the reaction system. In addition, the enamine derivative represented by formula IV may be prepared by reacting the β-diketone compound represented by formula V

   V wherein $R^1$ and $R^5$ have the same significance as in general formula I XVI and amine represented by the formula XVI

   XVI wherein R represents same significance as in general formual I and separating the product before use but the following method may of course be employed. That is, the compound of formula V is caused to react with substantially equimolar amount or excessive molar amount of the amine of general formula XVI in a reaction vessel preferably, in the presence of, an organic solvent such as ethanol to form the compound of general formula IV then the compound of general formula II and the compound of general formula III are added to the reaction mixture containing the compound of general formula IV without isolation to proceed reaction.

B. The compound represented by general formula II, the enamine compound represented by general formula VI

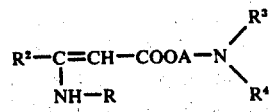   VI wherein R, $R^2$, $R^3$, $R^4$, and A have the same significance as in general formula I, and the compound represented by general formula V are reacted under the similar conditions as in method A). In addition, as in method A), the compound of general formula III may be caused to react with the amine of general formula XVI to form the compound of general formula VI and the compound of general formula II and the compound of general formula V may be added to the reaction mixture without isolating the compound of formula VI thus formed.

C. The compound of general formula II is first caused to react with the compound of formula III to form the lower alkanoylcinnamic acid alkyl ester represented by the formula VII

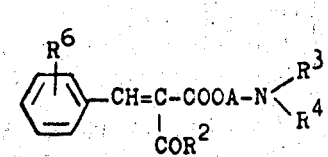   VII wherein $R^2$, $R^3$, $R^4$, $R^6$, and A have the same significance as in general formula I and then the product is caused to react with the compound of formula IV or alternatively the compound of formula II is first caused to react with the compound of formula V to form the compound represented by the formula VIII

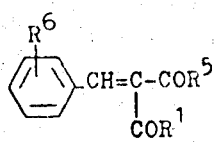  VIII

  XI wherein $R^1$, $R^5$, and $R^6$ have the same significance as in general formula I and then the product is caused to react with the compound of general formula VI.

D. The compound of formula VII is first prepared in a similar manner as shown in method C) and then the product is caused to react with the compound of formula V and the amine of general formula XV or alternatively, the compound of formula VIII is first prepared by the similar manner as in method C), and then the product is caused to react with the compound of formula III and the amine of formula XVI.

E. The compound of formula II, the compound of formula III, the compound of formula V, and the compound of formula XVI are reacted in equimolar ratio preferably, in an organic solvent.

In the case of producing the compound of formula VI or the compound of formula IV by reacting the compound of formula III or the compound of formula V with the compound of formula XVI in the aforesaid methods, it is preferable to use the compound of formula XVI in substantially equimolar amount or excessive amount to the compound of formula III or the compound of formula V and to add the compound of formula XVI, if necessary, as a solution thereof in an organic solvent such as methanol, ethanol, and the like to the reaction system. In addition, when an excessive amount of the compound of formula XVI is used, it is necessary that after the reaction is over, excessive compound of formula XVI is removed from the reaction mixture by a reduced-pressure concentration method, etc., and then the product is caused to react with other reactants, that is the compound of the formula II and the compound of formula III or the compound of formula II and the compound of formula V.

Moreover, the compounds of this invention may also be produced by the following procedures:

F. The compound of formula II, the compound of formula IV, and the compound represented by general formula IX

  IX wherein X represents a halogen atom and $R^2$ and A have the same significance as in general formula I are reacted to form the compound represented by formula X

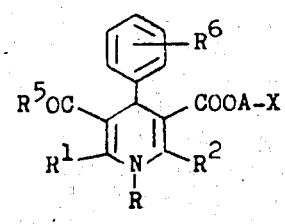  X wherein R, $R^1$, $R^2$, $R^5$, $R^6$, A, and X have the same significance as above and then the compound is caused to react with the amine represented by formula XI wherein $R^3$ and $R^4$ have the same significance as above or alternatively the compound of formula II, the compound of formula V, and the compound represented by formula XII

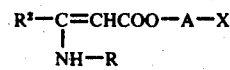  XII wherein R, $R^2$, A, and X have the same significance as above are reacted to provide the compound of formula X and then the product is caused to react with the compound of formula XI.

G. The compound represented by general formula XIII

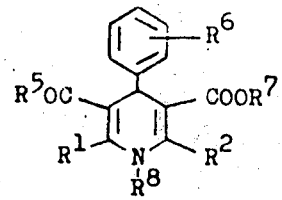  XIII wherein $R^7$ represents a lower alkyl group, $R^8$ represents a lower alkoxyalkyl group, and $R^1$, $R^2$, $R^5$, and $R^6$ have the same significance as above is first prepared, the product is caused to react with the amino alcohol represented by the general formula XIV

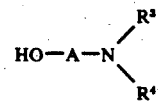  XIV wherein $R^3$ and $R^4$ have the same significance as above to provide the compound represented by general formula XV

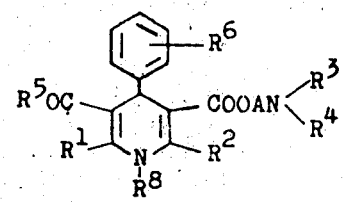  XV wherein A, R, $R^1$, $R^2$, $R^3$, $R^4$, $R^5$, $R^6$, and $R^8$ have the same significance as above. and the product is further hydrolyzed under acidic state to produce the compound by the general formula (I) wherein R is a hydrogen atom.

The above-mentioned processes are illustratives and the process of the present invention is not limited by these illustratives and some modifications of these processes are equally applicable in the present invention.

The subject products prepared by the aforesaid various methods can be isolated and purified by an ordinary chemical operation such as extraction, column chromatography, recrystallization, and the like.

The subject compounds of general formula I can be desirably converted into therapeutically innoxious salts, for example with mineral acid salts such as hydrochlorides, sulfates, phosphates, etc., or organic acid salts such as acetates, fumarates, maleates, tartarates, etc.

The salts of these compounds are suitable for liquid pharmaceutical preparations (especially injection), as these salts are highly soluble in water without using solubilizing agents.

The appropriate dose of the compound of this invention for human beings per ounce is 0.1–1.0 mg. in intravenous administration and 5–20 mg. in oral administration, two or three times a day are appropriate.

Now, examples of the lower alkyl group represented by R, $R^1$, $R^2$, $R^4$, and $R^5$ in the compounds of this invention represented by formula I

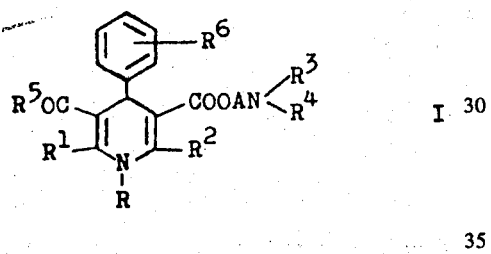

are a methyl group, an ethyl group, a propyl group, an isopropyl group, a n-butyl group, a tert-butyl group, a pentyl group, etc. and examples of the lower alkoxyl group represented by $R^5$ are a methoxy group, an ethoxy group, a propoxy group, an isopropoxy group, a n-butoxy group, an isobutoxy group, a tert-butoxy group, a pentyloxy group, etc. Also, examples of the lower alkoxyl group substituted by a lower alkoxyl group represented by $R^5$ are a methoxymethoxy group, a 2-methoxyethoxy group, a 2-ethoxyethoxy group, a 2-propoxyethoxy group, a 2-methoxypropoxy group, a 2-propoxypropoxy group, a 5-methoxypentyloxy group, a 3-methoxypentyloxy group, etc. Examples of the alkylene group represented by A in the aforesaid general formula I are a methylene group, an ethylene group, a trimethylene group, a tetramethylene group, a propylene group, an ethylethylene group, etc. Examples of the phenyl group, which may have a substituent, represented by $R^3$ are a phenyl group, an o-tolyl group, a m-tolyl group, a p-tolyl group, a 2,3-xylyl group, a mesityl group, a cumenyl group, an o-methoxyphenyl group, a m-methoxyphenyl group, p-methoxyphenyl group, an o-chlorophenyl group, an m-chlorophenyl group, a p-chlorophenyl group, an o-bromophenyl group, an m-bromophenyl group, a p-bromophenyl group, etc. Also, examples of the aralkyl group represented by $R^3$ are a benzyl group, a phenetyl group, etc., and further examples of the substituent of the aralkyl group are a lower alkyl group such as a methyl group, an ethyl group, etc.; a lower alkoxy group such as a methoxy group, a propoxy group, etc., and a halogen atom such as a chlorine atom, a bromine atom, etc.

Illustrative examples of the compounds prepared by the process of this invention are as follows:

2,6-Dimethyl-4-(3'-nitrophenyl)-1,4-dihydropyridine-3,5-dicarboxylic acid 3-β-(N-benzyl-N-methylamino)ethyl ester 5-methyl ester 2,6-Dimethyl-4-(3'-nitrophenyl)-1,4-dihydropyridine-3,5-dicarboxylic acid 3-β-(N-benzyl-N-methylamino)ethyl ester 5-ethyl ester 2,6-Dimethyl-4-(3'-nitrophenyl)-1,4-dihydropyridine-3,5-dicarboxylic acid 3-β-(N-benzyl-N-methylamino)ethyl ester 5-isopropyl ester 2,6-Dimethyl-4-(2'-nitrophenyl)-1,4-dihydropyridine-3,5-dicarboxylic acid 3-β-(N-benzyl-N-methylamino)ethyl ester 5-isopropyl ester 2,6-Dimethyl-4-(3'-nitrophenyl)-1,4-dihydropyridine-3,5-dicarboxylic acid 3-β-(N-benzyl-N-ethylamino)ethyl ester 5-isopropyl ester 2,6-Dimethyl-4-(3'-nitrophenyl)-1,4-dihydropyridine-3,5-dicarboxylic acid 3-β-(N-benzyl-N-methylamino)propyl 5-ester isopropyl ester 2,6-Dimethyl-4-(3'-nitrophenyl)-1,4-dihydropyridine-3,5-dicarboxylic acid 3-β-(N-p-methoxybenzyl-N-methylamino)ethyl ester 5-isopropyl ester 2,6-Dimethyl-4-(3'-nitrophenyl)-1,4-dihydropyridine-3,5-dicarboxylic acid 3-β-(N-p-chlorobenzyl-N-methylamino)ethyl ester 5-ethyl ester 3-Acetyl-2,6-dimethyl-4-(3'-nitrophenyl)-1,4-dihydropyridine-5-carboxylic acid 3-β-(N-benzyl-N-methylamino)ethyl ester 3-Acetyl-2,6-dimethyl-4-(3'-nitrophenyl)-1,4-dihydropyridine-5-carboxylic acid 3-β-(N-p-chlorobenzyl-N-methylamino)ethyl ester 2,6-Dimethyl-4-(2'-trifluoromethylphenyl)-1,4-dihydropyridine-3,5-dicarboxylic acid bis ]β-(N-o-chlorobenzyl-N-ethylamino)ethyl] ester dihydrobromide 4-(2'-Trifluoromethylphenyl)-2,6-dimethyl-3-propionyl-1,4-dihydropyridine-5-carboxylic acid 3-β-(N-ethyl-N-p-methoxyphenylamino)methyl ester 3-Acetyl-2,6-diethyl-4-(2'-nitrophenyl)-1,4-dihydropyridine-5-carboxylic acid 3-β-(N-p-chlorophenyl-N-methylamino)ethyl ester hydrochloride 2,6-Dimethyl-4-(3'-nitrophenyl)-1,4-dihydropyridine-3,5-dicarboxylic acid bis [β-(N-benzyl-N-methylamino)ethyl] ester dihydrochloride 2,6-Dimethyl-4-(2'-nitrophenyl)-1,4-dihydropyridine-3,5-dicarboxylic acid 3-β-(N-methyl-N-p-tolylmethylamino)ethyl ester 5-(2-propoxy)ethyl ester hydrochloride The results of the cerebral vasodilating activity of the present compounds are shown in the following table.

Method: Adult mongrel dogs were anesthethized with sodium pentobarbital (30 mg/Kg, i.v.) and were artificially ventilated. Vertebral blood flow was measured with an electromagnetic flowmeter (Nihon Kohden Co., Ltd. MF-5) positioned around the vessel. $LD_{50}$ was determined by using mice. The results are shown in the following table.

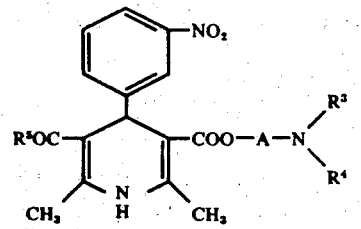

| Sample | | | | Vertebral blood flow effective dose(mg/Kg,i.v.) | LD$_{50}$ (mg/Kg,i.v.) |
|---|---|---|---|---|---|
| R$^5$ | A | R$^3$ | R$^4$ | | |
| CH$_3$O— | —CH$_2$CH$_2$— | ⟨phenyl⟩—CH$_2$— | CH$_3$— | 0.0003 – 0.01 | 20.7 |
| C$_2$H$_5$O— | " | " | " | " | 15 |
| (CH$_3$)$_2$CHO— | | | | | |
| " | " | " | C$_2$H$_5$— | " | 12 |
| " | —CH$_2$CH$_2$CH$_2$— | " | CH$_3$— | " | 10 |
| C$_2$H$_5$O— | —CH$_2$CH$_2$— | CH$_3$O—⟨phenyl⟩—CH$_2$— | " | " | 10 |
| " | " | Cl—⟨phenyl⟩—CH$_2$— | " | " | 12 |
| CH$_3$— | " | ⟨phenyl⟩—CH$_2$— | " | 0.001 – 0.01 | 40 |
| " | " | Cl—⟨phenyl⟩—CH$_2$— | " | " | 45 |
| Nifedipine | | | | 0.001 – 0.01 | 5.6 |

The following pharmacological data represents the cerebral vasodilating activity, spasmolytic activity and acute toxicity of one of our compounds, 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride (hereinafter called as compound A) in comparison with those of papaverine and nifedipine.

1. Effect on the cerebral circulation, heart rate and blood pressure after intravenous injection:

Methods: Adult mongrel dogs were anesthethized with sodium pentobarbital (30 mg/Kg, i.v.) and were artificially ventilated. Vertebral blood flow was measured with an electromagnetic flowmeter (Nihon Kohden Co., Ltd. MF-5) positioned around the vessel. Blood pressure at the femoral artery was measured by a pressure transducer (Nihon Kohden Co., Ltd. MPU-0.5) and heart rate by a cardiotachometer (Nihon Kohden Co., Ltd. RT-2). All drugs were given into the femoral vein.

Results: Effects of the compound A, papaverine and nifedipine on vertebral blood flow, mean blood pressure and heart rate in anesthethized dogs were shown in the following table.

Table

| Drugs | Dose (mg/Kg i.v.) | No. of animals | Vertebral blood flow (Δ%±SE) | Mean blood pressure (ΔmmHg±SE) | Heart rate (Δbeats/min.±SE) |
|---|---|---|---|---|---|
| Papaverine | 0.1 | 8 | 22±3.4 | −9±1.1 | 8±1.5 |
| | 0.3 | 8 | 67±7.1 | −21±2.8 | 22±3.5 |
| | 1.0 | 8 | 124±13.8 | −32±3.5 | 44±4.8 |
| Nifedipine | 0.001 | 5 | 47±13.5 | −10±1.6 | 10±3.5 |
| | 0.003 | 4 | 104±25.8 | −24±5.9 | 18±3.2 |
| | 0.01 | 6 | 135±28.8 | −39±3.2 | 17±4.0 |
| Compound A | 0.0003 | 8 | 27±4.4 | −1±0.6 | 4±1.3 |
| | 0.001 | 8 | 61±9.5 | −7±1.5 | 12±2.2 |
| | 0.003 | 8 | 132±13.8 | −14±2.2 | 18±2.0 |
| | 0.01 | 8 | 200±27.3 | −29±3.6 | 25±5.3 |

2. Direct effect on cerebral and femoral arteries:

For the analysis of the selective effect on vasculature by the drugs, direct effect on cerebral (vertebral artery) and peripheral (femoral artery) vascular bed were studied by the method of the constant volume perfusion.

Method: Adult mongrel dogs were anesthetized with sodium pentobarbital (30 mg/Kg, i.v.) and artificially ventilated. Heparin (1000 μ/Kg, i.v.) was used as an anticoagulant. The methods for perfusion of each artery were as following: 1) For the vertebral artery, the arterial blood led from the left common carotid artery was collected by the tygon tubing and perfused by the Sigma-motor pump (Mippleport N.Y. T-8) into the right vertebral artery. 2) For the femoral artery, the arterial blood led from the proximal femoral artery was perfused by the Sigma-motor pump into the distal femoral artery. Vascular responses were expressed as changes in perfusion pressure which was measured by the pressure transducer (Nihon Kohden Co., Ltd. MPU-0.5). All drugs were given into a rubber tube connected close to the each arterial cannula by a microinjector (Jintan Terumo, NSN-100). Dose response curve of each drug was determined and 50% effective dose (ED50) of each drug was obtained, when the maximum responses to papaverine at 3000 μg i.a. was expressed as 100% response.

Results: Effects of intra-arterially administered papaverine, nifedipine and compound A on vertebral and femoral artery were shown in the following table.

| Drugs | No. of animals | Vasodilation $ED_{50}\mu g \pm SE$ Vertebral artery | Femoral artery | Selectivity ratio ($ED_{50}$ in femoral artery /$ED_{50}$ in vertebral artery) |
|---|---|---|---|---|
| Papaverine | 4 | 72.8±8.71 | 48.8±3.73 | 0.67 |
| Nifedipine | 4 | 0.74±0.15 | 0.37±0.11 | 0.50 |
| Compound A | 4 | 0.66±0.20 | 0.86±0.11 | 1.30 |

3. Spasmolytic activity:

Methods: Isolated guinea-pig ileum was suspended in Tyrodes solution by use of Magnus apparatus and the movements of the muscle were recorded in a kymograph by an isotonic lever. Barium chloride, acetylcholine and histamine were used as an agonist and 50% inhibition by the antagonist was measured regarding the contractile responses to the antagonist.

Results:

Table

| Antagonist | Concentration (g/ml) | Spasmolytic activity (g/ml±S.E) Papaverine | Nifedipine | Compound A |
|---|---|---|---|---|
| $BaCl_2$ | $2\times 10^{-4}$ | $7.2\pm 0.2\times 10^{-6}$ | $3.3\pm 0.2\times 10^{-9}$ | $1.9\pm 0.4\times 10^{-9}$ |
| Acetylchloline | $10^{-7}$ | $1.1\pm 0.1\times 10^{-5}$ | $1.6\pm 1.1\times 10^{-8}$ | $5.2\pm 10\times 10^{-9}$ |
| Histamine | $10^{-7}$ | $7.0\pm 1.9\times 10^{-6}$ | $5.5\pm 0.9\times 10^{-8}$ | $1.8\pm 0.2\times 10^{-9}$ |

4. Acute toxicity:

Comparison of the intravenous acute toxicity between compound A and nifedipine was accomplished by using ICR-male mice and mongrel dogs.

Table

| Sample | $LD_{50}$ (mg/Kg,i.v.) Mice | Dogs |
|---|---|---|
| Compound A | 20.7 | 6.1 |
| Nifedipine | 5.6 | 1.5 |

From the above results, the compounds of this invention have potent spasmolytic activity, potent and selective cerebral vasodilating activity and low toxicity.

5. Solubility in water

The water-solubility (at 25° c) of the compound of this invention and known compounds of prior art is shown in the following table.

| Known Compounds | Solubility % | pH | Solubility (%) at pH 4.00 |
|---|---|---|---|
| Nifedipine[4-(2'-nitrophenyl-2,6-dimethyl-1,4-dihydropyridine-3,5-dicarboxylic acid dimethyl ester: example 1 of U.S. Patent No. 3,485,847 or No. 3,644,627] | 0.001 | 5.40 | 0.001 |
| 4-(3'-nitrophenyl)-2,6-dimethyl-3.5-di-(carbocylic acid β-propoxyethyl ester)-1,4-dihydropyridine (U.S. Patent No. 3,488,359 example 9) | *1 | | |
| 3,5-dicarbethoxy-1,4-dihydro-2,6-dimethyl-4-(2-trifluromethylphenyl) pyridine (U.S. Patent No. 3,511,847 example 1, SKF 24260) | 0.001 | 5.40 | 0.001 |
| 4-(2'-cyanophenyl)-2,6-dimethyl-1,4-dihydropyridine-dicarboxylic acid dimethyl ester (U.S. Patent No. 3,691,177 example 1e) | 0.001 | 5.80 | 0.0001 |

*1: 0.0008mg/ml i.e. 0.00008%; J. Pharm. Sci., 61, (10) 1686 (1972)

| The Compound of the Present Invention | Solubility % | pH |
|---|---|---|
| 2,6-dimethyl-4-(3'-nitrophenyl)-1,4-dihydropyridine-3,5-dicarboxylic acid-3-isopropyl ester -5-β-(N-benxyl-N-methylamine) ethyl ester hydrochloride (example 1) | 0.31 | 4.12 |
| 2,6-dimethyl-4-(3'-nitrophenyl)-1,4-dihydropyridine-3,5-dicarboxylic acid-3-methyl ester 5-β-(N-benzyl-N-methylamino) ethyl ester hydrochloride (example 2) | 0.49 | 3.92 |
| 2,6-dimethyl-4-(2'nitrophenyl)-1,4-dihydropyridine-3,5-dicarboxylic acid-3-isopropyl ester-5-β-N-benzyl-N-methylamino) ethyl ester hydrochloride (example 4) | 0.32 | 4.10 |
| 2,6-dimethyl-4-(3'-nitrophenyl)-1,4-dihydropyridine-3,5-dicarboxylic acid 3-ethyl ester 5-β-(N-benzyl-N-methylamino) ethyl ester hydrochloride (example 6) | 0.29 | 4.20 |
| 2,6-dimethyl-4-(2'-nitrophenyl)-1,4-dihydropyridine-3,5-dicarboxylic acid bis[β-N-benzyl-N-methylamino ethyl] ester hydrochloride (example 9) | 2.74 | 3.16 |
| 2,6-dimethyl-4-(3'-nitrophenyl)-1,4-dihydropyridine-3,5-dicarboxylic acid 3-ethyl ester 5-β-(N-methyl-N-p-methoxybenxylamino) ethyl ester hydrochloride (example 14) | 0.10 | 4.17 |
| 2,6-dimethyl-4-(3'-nitrophenyl)-1,4-dihydropyridine-3,5-dicarboxylic acid bis [β-N-methyl-N-p-methoxyphenylamino) ethyl] ester dihydrochloride (example 16) | 2.53 | 3.20 |
| 2,6-dimethyl-4-(2'-trifluoromethylphenyl)-1,4-dihydropyridine-3,5-dicarboxylic acid 3-methyl ester 5-β-(N-benxyl-N-methylamino) | 0.23 | 3.91 |

-continued

| The Compound of the Present Invention | Solubility | |
|---|---|---|
| | % | pH |
| ethyl ester hydrochloride (example 24) | | |

As shown above, the compounds of this invention have excellent water-solubility in comparison with known dihydropyridine derivatives (that is, even the lowest solubility of the compounds of this invention shows a value 100 times as much as the known compounds.). Therefore, the compounds of this invention are suitable for preparing injection solution.

6. The comparision of blood flow increasing effective and lethal doses

1. Vertebral and femoral blood flow in anesthetized dogs.

Mongrel dogs of both sexes weighing from 12 to 27 kg were anesthetized with sodium pentobarbitol (30 mg/kg i.v.). In all experiments, trachea was cannulated and the animals were artificially ventilated with room air. Blood pressure in cannulated femoral artery was measured by means of a pressure transducer (Nihon Kohden, MPU 0.5). Vertebral and femoral blood flow were measured by a noncannulating electromagnetic flowmeter (Nihon Kohden, MF-25) positioned around the vessels. Recordings were made on an ink-writing polygraph (Nihon Kohden, RM-150 or RM-85). The test compounds were injected at a dose of 0.01 mg/kg into femoral vein.

2. Acute toxicity in mice

Male ICR weighing 25 to 32 g were used. The test compounds were injected into tail vein and $LD_{50}$ values were determined. The result is shown in the following table.

blood flow were approximately 1, indicating that they had no specific effect on these vascular beds.

On the other hand, the compounds of the present invention, in a dose of 0.01 or 0.03 mg/kg i.v., increased vertebral blood flow more intensely than femoral blood flow. The separation ratios of the compounds of the present invention were significantly larger than that of SKF-24260, indicating that they exerted preferential effect for the vertebral artery as opposed to the vessels supplied to the hind quarter.

It was reported that approximately 70 percent of cerebral blood flow was derived via vertebral arteries (Rittmann, W. W. and Smith, L. L. Surg. Gynec. Obst. 67, 67, 1966) and the vertebral blood flow was likely to indicate the cerebral blood flow (Yamane, Y., Jap. Circul. J. 23 633 1959). Then, present results indicate that the compounds of the present invention have a selective vasodilator effect on cerebral vascular bed as compared with known compound tested.

Furthermore, $LD_{50}$ values of the compounds of the present invention were apparently lower than those of known compounds in mice. These data indicate that the new compounds have a significant safety margin between the effective and toxic doses as compared with known compounds.

The compounds of this invention are suitable for preparing into injections, as these compounds are highly soluble in water and have low toxicity. Further, these compounds show remarkably increased absorption amounts upon oral administration. The side effects such as increase of heart-rate or change of electrocardiogram found in known compounds are not found in the compounds of this invention.

Therefore, they are useful for the treatment of acute stroke from occlusive cerebral vascular disease and apoplexy and postapopletic condition from cerebral

| KNOWN COMPOUNDS | | Flow (VBF Δ %) | Flow (FBF %) | | | Δ mmH, | $LD_{50}/K$, i.v. |
|---|---|---|---|---|---|---|---|
| 3,5-dicarbethoxy-1,4-dihydro-2,6-dimethyl-4-(2-trifluromethylphenyl) pyridine (U.S. Patent No. 3,511,847, example 1, SKF 24260) | 6 | 144 ± 17.7 | 165 ± 40 | 0.93 ± 0.11 | | −44 ± 4.8 | 0.8 |
| Nifcolipine[4-(2'-nitrophenyl-2,6-dimethyl-1,4-dihydropyridine-3,5-dicarboxylic acid dimethyl ester :example 1 of U.S. Patent No. 3,485,847 or 3,644,627] | 9 | 135 ± 28.8 | 109 ± 34.1 | 1.14 ± 0.36 | (N.S.)[-1] | −39 ± 3.2 | 5.6 |
| 4-(2'-cyanophenyl)2,6-dimethyl-1,4-dihydropyridine-dicarboxylic acid dimethyl ester (U.S. Patent No. 3,691,177 example 1e) | 6 | 97 ± 16.0 | 109 ± 28.0 | 1.20 ± 0.27 | (N.S.) | −38 ± 6.0 | 7.4 |
| COMPONENTS OF THE PRESENT INVENTION | | | | | | | |
| 2,6-dimethyl-4-(3'-nitrophenyl)-1,4-dihydropyridine-3,5-dicarboxylic acid 3-methyl ester 5-β-(N benzyl-N-methylamino) ethyl ester hydrochloride (example 2) | 8 | 200 ± 27.3 | 51 ± 5.8 | 4.19 ± 0.69 | (p < 0.01) | −29 ± 3.6 | 20.7 |
| 2,6-dimethyl-4-(2'-trifluromethylphenyl)-1,4-dihydropyridine-3,5-dicarboxylic acid 3-methyl ester 5-β(N-benxyl-N-methylamino) ethyl hydrochloride (example 24) | 6 | 119 ± 20.4 | 67 ± 10.5 | 2.04 ± 0.53 | (p < 0.05) | −28 ± 4.9 | 23.7 |
| 2,6-dimethyl-4-(2'-nitrophenyl)-1,4-dihydropyridine-3,5-dicarboxylic acid 3-methyl ester 5-β-(N-benxyl-N-methylamino) ethyl ester hydrochloride (example 36) | 4 | 167 ± 31.7 | 83 ± 14.1 | 2.21 ± 0.56 | (p < 0.05) | −26 ± 5.0 | 14.0 |

[-1] Figures in parenthese indicate the significance in comparison with SKF 24260, N.S. means no significance.

Results and comments

As shown in Table, all of the known compounds tested in a dose of 0.01 mg/kg i.v., increased vertebral and femoral blood flow almost the same extent in anesthetized dogs. The separation ratios of these compounds which were calculated by dividing the percent increase of vertebral blood flow by that of femoral vascular disorders by both injection and long-term oral administration.

EXAMPLE 1

A mixture of 5 g. of acetoacetic acid β-(N-benzyl-N-methylamino) ethyl ester, 2.8 g. of β-aminocrotonic acid isopropyl ester, and 3 g. of m-nitrobenzaldehyde was stirred for 6 hours at 100° C in an oil bath. Then, by treating the product as in Example 2 shown below, 2.5 g. of 2,6-dimethyl-4-(3'-nitrophenyl)-1,4-dihydropyridine-3,5-dicarboxylic acid-3-isopropylester-5-β-(N-benzyl-N-methylamino)-ethyl ester hydrochloride was obtained.

Elemental Analysis for $C_{28}H_{34}N_3O_6Cl$:

|  | C(%) | H(%) | N(%) | Cl(%) |
|---|---|---|---|---|
| Calculated: | 61.82 | 6.30 | 7.72 | 6.52 |
| Found: | 61.58 | 6.15 | 7.42 | 6.50 |

EXAMPLE 2

A mixture of 4.98 g. of acetoacetic acid N-benzyl-N-methylaminoethyl ester, 2.3 g. of β-aminocrotonic acid methyl ester, and 3 g. of m-nitrobenzaldehyde was stirred for 6 hours at 100° C in an oil bath. The reaction mixture was subjected to a silica gel column chromatography (diameter 4 cm. and height 25 cm.) and then eluted with a 20 : 1 mixture of chloroform and acetone. The effluent containing the subject product was concentrated and checked by thin layer chromatography. The powdery product thus obtained was dissolved in acetone and after adjusting the solution with an ethanol solution saturated with hydrogen chloride to pH 1-2, the solution was concentrated to provide 2g. of 2,6-dimethyl-4-(3'-nitrodiphenyl)-1,4-dihydropyridine-3,5-dicarboxylic acid 3-methylester-5-β-(N-benzyl-N-methylamino)-ethyl ester hydrochloride. The product thus obtained was then crystallized from an acetone mixture, Melting point: 136°–140° C. (decomposed)
Elemental Analysis for $C_{26}H_{30}N_3O_6Cl$:

|  | C(%) | H(%) | N(%) | Cl(%) |
|---|---|---|---|---|
| Calculated: | 60.52 | 5.86 | 8.14 | 6.87 |
| Found: | 60.25 | 5.87 | 7.88 | 6.67 |

EXAMPLE 3

A mixture of 4.2 g. of acetoacetic acid β-(N-methyl-N-phenylamino)ethylester, 2.05 g. of β-aminocrotonic acid methyl ester, and 2.68 g. of m-nitrobenzaldehyde was stirred for 5 hours at 100° C, in an oil bath. The reaction mixture was subjected to a silica gel column chromatography (diameter 4 cm., height 25 cm) and then eluted with a chloroform-acetone mixture of 20 : 1 by volume ratio. The effluent was checked by thin layer chromatography, the effluent containing the subject product was collected and concentrated under reduced pressure, the subject product was crystallized. The crystals were collected and recrystallized from a mixture of ether and petroleum ether to provide 0.9 g. of 2,6-dimethyl-4-(3'-nitrophenyl)-1,4-dihydropyridine-3,5-dicarboxylic acid 3-methylester-5-β-(N-methyl-N-phenyl)aminoethyl ester.

Melting point: 135°–138° C.
Elemental analysis for $C_{25}H_{27}N_3O_6$:

|  | C(%) | H(%) | N(%) |
|---|---|---|---|
| Calculated: | 64.50 | 5.85 | 9.03 |

-continued

|  | C(%) | H(%) | N(%) |
|---|---|---|---|
| Found: | 64.48 | 5.81 | 8.95 |

EXAMPLE 4

In 3 ml. of isopropanol were dissolved 4.4 g. of acetoaceticac β-(N-benzyl-N-methylamino)ethyl ester, 2.6 g. of β-aminocrotonic acid isopropyl ester, and 2.7 g. of o-nitrobenzaldehyde and then the solution thus prepared was heated for 5 hours to 80° C. The reaction mixture was dissolved in 50 ml. of chloroform and then the solution was washed with 20 ml. of 10% hydrochloric acid and 20 ml. of water and further with 30 ml. of 10% aqueous sodium hydroxide solution and 20 ml. of water. The chloroform layer thus formed was separated, dried over anhydrous magnesium sulfate, and then chloroform was distilled off under reduced pressure. The residue formed was dissolved in a small amount of chloroform and the solution prepared was subjected to a silica gel column chromatography (diameter 3 cm., height 20 cm.). The product was eluted with a chloroform-acetone mixture of 20 : 1 by volume ratio. The effluent was checked with a thin layer chromatography and the effluent containing the aimed product was collected and was concentrated under reduced pressure to provide 2.2 g. of 2,6-dimethyl-4-(2'-nitrophenyl)-1,4-dihydropyridine-3,5-dicarboxylic acid 3-isopropylester-5-β-(N-benzyl-N-methylamino)ethyl ester. The product was dissolved in acetone and after neutralizing the solution with ethanol saturated with hydrogen chloride, the solution was concentrated under reduced pressure to provide the hydrochloride of the aforesaid compound.

Melting point: 208°–210° C. (decomposed)
Elemental analysis for $C_{28}H_{34}N_3O_6Cl$:

|  | C(%) | H(%) | N(%) | Cl(%) |
|---|---|---|---|---|
| Calculated: | 61.82 | 6.30 | 7.72 | 6.52 |
| Found: | 61.63 | 6.25 | 7.65 | 6.73 |

EXAMPLE 5

In 5 ml. of isopropanol were dissolved 5.0 g. of acetoacetic acid γ-(N-benzyl-N-methylamino)propyl ester, 2.7 g. of β-aminocrotonic acid isopropyl ester, and 2.9 g. of m-nitrobenzaldehyde and the solution was heated to 80° C. for 5 hours.

Then, by treating the reaction mixture thus obtained as in below showing Example 4, 3.1 g. of 2,6-dimethyl-4-(3'-nitrophenyl)-1,4-dihydropyridine-3,5-dicarboxylic acid 3-isopropylester-5-γ-(N-benzyl-N-methylamino)propyl ester was obtained. The melting point of the hydrochloride of this compound was 166°–169° C. (decomposed).

Elemental analysis for $C_{29}H_{36}N_3O_6Cl$:

|  | C(%) | H(%) | N(%) | Cl(%) |
|---|---|---|---|---|
| Calculated: | 62.41 | 6.50 | 7.53 | 6.35 |
| Found: | 62.35 | 6.39 | 7.41 | 6.55 |

EXAMPLE 6

In 3 ml. of isopropanol were dissolved 4.0 g. of acetoacetic acid β-(N-benzyl-N-methylamino)ethyl ester, 2.1 g. of β-aminocrotonic acid ethyl ester, and 2.4 g. of m-nitrobenzaldehyde and then the solution was heated to 80° C. for 5 hours.

Then, by treating the product thus obtained as in Example 4, 1.5 g. of 2,6-dimethyl-4-(3'-nitrophenyl)-1,4-dihydropyridine-3,5-dicarboxylic acid 3-ethylester-5-β-(N-benzyl-N-methylamino)ethyl ester. The results of the elemental analysis of the hydrochloride of the product are shown below:

Elemental analysis for $C_{27}H_{32}N_3O_6Cl$:

|  | C(%) | H(%) | N(%) | Cl(%) |
|---|---|---|---|---|
| Calculated: | 61.19 | 6.09 | 7.93 | 6.69 |
| Found: | 61.43 | 6.33 | 7.66 | 6.59 |

EXAMPLE 7

In 6 ml. of isopropyl alcohol were dissolved 2.6 g. of β-aminocrotonic acid, β-(N-benzyl-N-methylamino)ethyl ester, 1.1 g. of methyl acetoacetate, and 1.5 g. of m-nitrobenzaldehyde and the solution prepared was stirred for 6 hours at 85° C.

The reaction mixture was cooled, dissolved in 10 ml. of chloroform, and then the solution was washed once with excessive dilute hydrochloric acid and then three times each with 7 ml. of water. Then, the chloroform layer thus formed was dried over anhydrous magnesium sulfate, and then chloroform was distilled off. When the residue was mixed with 15 ml. of ethyl acetate followed by stirring, the product was crystallized, which was separated, dried and recrystallized from acetone to provide 2.4 g. of the crystals of 2,6-dimethyl-4-(3'-nitrophenyl)-1,4-dihydropyridine-3,5-dicarboxylic acid 3-methylester-5-β-(N-benzyl-N-methylamino)ethyl ester hydrochloride.

Melting point: 128°–132° C. (decomposed)

Elemental analysis for $C_{26}H_{30}N_3O_6Cl \cdot \frac{1}{2}CH_3COCH_3$:

|  | C(%) | H(%) | N(%) | Cl(%) |
|---|---|---|---|---|
| Calculated: | 60.60 | 6.10 | 7.71 | 6.50 |
| Found: | 60.61 | 6.14 | 7.46 | 6.71 |

EXAMPLE 8

In 20 ml. of isopropyl alcohol were dissolved 5.0 g. of β-aminocrotonic acid β-dimethylaminoethyl ester, 7.2 g. of acetoacetic acid (N-benzyl-N-methylamino)ethyl ester, and 4.3 g of m-nitrobenzaldehyde and then the solution formed was stirred for 5 hours at 85° C. After the reaction was over, the reaction mixture was cooled, dissolved in 50 ml. of ethyl acetate, and then the product was extracted once with excessive hydrochloric acid and then three times each with 50 ml. of water. The whole extracts were combined with each other and after basifying the solution with a dilute aqueous solution of sodium hydroxide, the product was extracted with chloroform. The cloroform extract was dried over anhydrous magnesium sulfate, concentrated, purified by means of a silica gel column chromatography using ethyl actetate as the effluent, and then the resulting fractions were collected. The fractions were concentrated, acidified with ethanolic hydrochloride acid, and then the solvent was distilled off to provide 4.0 g. of the crystalline powder of 2,6-dimethyl-4-(3'-nitrophenyl)-1,4-dihydropyridine-3,5-dicarboxylic acid 3-β-(N-benzyl-N-methylamino) ethyl ester 5-(β-N,N-dimethylamino)ethyl ester.

Elemental Analysis for $C_{29}H_{38}N_4O_6Cl_2$:

|  | C(%) | H(%) | N(%) | Cl(%) |
|---|---|---|---|---|
| Calculated: | 57.14 | 6.28 | 9.18 | 11.63 |
| Found: | 57.02 | 6.56 | 8.93 | 11.83 |

EXAMPLE 9

In 12 ml. of isopropyl alcohol were dissolved 4.0 g. of acetoacetic acid β-(N-benzyl-N-methylamino) eithyl ester, 1.22 g. of m-nitrobenzaldehyde, and 1.3 ml. of ammonia water and the solution formed was stirred for 6 hours at 85° C. Then, by treating the reaction mixture thus obtained as in Example 8, 3.0 g. of the crystalline powder of 2,6-dimethyl-4-(2'-nitrophenyl)-1,4-dihydropyridine-3,5-dicarboxylic acid bis[β-(N-benzyl-N-methylaminethyl] ester hydrochloride.

Elemental Analysis for $C_{35}H_{42}N_4O_6Cl_2$:

|  | C(%) | H(%) | N(%) | Cl(%) |
|---|---|---|---|---|
| Calculated: | 61.31 | 6.17 | 8.17 | 10.34 |
| Found: | 61.06 | 6.20 | 7.95 | 10.22 |

EXAMPLE 10

In 7 ml. of isopropanol were dissolved 2.2 g. of acetoacetic acid β-chloroethyl ester, 6.6 g. of m-nitrobenzaldehyde, and 5.2 g. of β-aminocrotonic acid ethyl ester and the solution was heated to 80° C for 4 hours. The reaction mixture was cooled, the crystals thus formed were collected by filtration and recrystallized from methanol to provide 3.5 g. of 2,6-dimethyl-4-(3'-nitrophenyl)-1,4-dihydropyridine-3,5-dicarboxylic acid 3-β-chloroethyl ester 5-ethyl ester Melting point: 164°–165° C.

Elemental analysis for $C_{19}H_{21}N_2O_6Cl$:

|  | C(%) | H(%) | N(%) | Cl(%) |
|---|---|---|---|---|
| Calculated: | 55.76 | 5.16 | 6.85 | 8.69 |
| Found: | 55.55 | 5.00 | 6.58 | 8.83 |

EXAMPLE 11 a. In 5 ml. of isopropanol were dissolved 3.0 g. of β-chloroethyl acetoacetate, 3.3 g. of m-nitrobenzaldehyde, and 2.3 g, of methyl β-aminocrotonate and the solution was heated to 80° C. for 4 hours.

The reaction mixture thus prepared was concentrated under reduced pressure, the residue was dissolved in a small amount of ethyl acetate, the solution was subjected to a silica gel column chromatography (diameter 3.3 cm., height 20 cm.), and then the product was eluted with ethyl acetate. The effluents containing the subject product were collected and concentrated to provide 2.0 g. of 2,6-dimethyl-4-(3'-nitrophenyl)-1,4-dihydropyridine-3,5-dicarboxylic acid 3-β-chloroethyl ester 5-methyl ester.

Melting point: 130°–131° C.

Elemental analysis for $C_{18}H_{19}N_2O_6Cl$:

|  | C(%) | H(%) | N(%) | Cl(%) |
|---|---|---|---|---|
| Calculated: | 54.76 | 4.85 | 7.10 | 8.98 |
| Found: | 54.43 | 4.74 | 6.91 | 9.18 | b. In 6 ml. of toluene were dissolved 2.0 g. of 2,6-dimethyl-4-(3′-nitrophenyl)-1,4-dihydropyridine-3,5-dicarboxylic acid 3-β-chloroethyl ester 5-methyl ester and 1.3 g. of N-methylbenzylamine and the solution thus formed was refluxed for 5 hours under heating. After the reaction was over, the reaction mixture was mixed with 30 ml. of chloroform and 10 ml. of water and then the organic layer thus formed was separated and washed with 10 ml. of 10% hydrochloric acid and then with water. The organic solvent solution thus obtained was dried over anhydrous magnesium sulfate and then the solvent was distilled away under reduced pressure. The residue was added to 10 ml. of ethyl acetate and the mixture was stirred under cooling, whereby 2,6-dimethyl-4-(3′-nitrophenyl)-1,4-dihydropyridine-3,5-dicarboxylic acid 3-β-(N-benzyl-N-methylamino)ethyl ester 5-methyl ester hydrochloride was crystallized. The amount of the product thus obtained was 1.6 g. The product recrystallized from a methanol-acetone mixture had a melting point of 180°–181° C.

Elemental analysis for $C_{26}H_{30}N_3O_6Cl$:

|  | C(%) | H(%) | N(%) | Cl(%) |
|---|---|---|---|---|
| Calculated: | 60.52 | 5.86 | 8.14 | 6.87 |
| Found: | 60.35 | 5.87 | 7.90 | 6.67 | c. In 6 ml. of toluene were dissolved 2.0 g. of 2,6-dimethyl-4-(3′-nitrophenyl)-1,4-dihydropyridine-3,5-dicarboxylic acid 3-β-chloroethyl ester 5-methyl ester 1.2 g. of benzylamine, and the solution was refluxed for 3 hours. After the reaction was over, the reaction mixture was mixed with 30 ml. of chloroform and 10 ml. of water and then the organic layer thus formed was separated, dried over anhydrous magnesium sulfate, and distilled under reduced pressure to remove the solvent. The residue was subjected to a silica gel column chromatography (diameter 4 cm., height 25 cm.) and the product was eluted using a mixture of benzene and acetone in 10 : 1 volume ratio. The effluent containing the subject product was checked with a thin layer chromatography, collected and concentrated under reduced pressure to give 0.8 g. of the crystalline powder of 2,6-dimethyl-4-(3′-nitrophenyl)-1,4-dihydropyridine-3,5-dicarboxylicacid 3-methyl ester β-(N-benzylamino)ethyl ester-5-methyl ester.

Elemental analysis for $C_{25}H_{27}N_3O_6$:

|  | C(%) | H(%) | N(%) |
|---|---|---|---|
| Calculated: | 64.50 | 5.85 | 9.03 |
| Found: | 64.41 | 5.72 | 8.85 |

The hydrochloride of the product prepared by treating it with alcoholic hydrochloric acid showed a melting point of 128–130° C. (decomposed).

EXAMPLE 12 a. In 10 ml. of isopropanol were dissolved 3.32 g. of acetoacetic acid β-chloroethyl ester, 3.0 g. of m-nitrobenzaldehyde, and 2.86 g. of β-aminocrotonic acid isopropyl ester and the solution was refluxed for 5 hours. The reaction mixture was concentrated and the residue was subjected to a silica gel chromatography. Then, the product was eluted therefrom using a mixture of chloroform and acetone in 10 : 1 volume ratio, the effluents containing the product were collected the solvent was distilled away from the solution, and the crystals thus formed were recrystallized from chloroform-ether mixture to provide 2.5 g. of 2,6-dimethyl-4-(3′-nitrophenyl)-1,4-dihydropyridine-3,5-dicarboxylic acid 3-β-chloroethyl ester 5-isopropyl ester.

Melting point: 140°–145° C.

Elemental analysis for $C_{20}H_{25}N_2O_6Cl$:

|  | C(%) | H(%) | N(%) | Cl(%) |
|---|---|---|---|---|
| Calculated: | 56.81 | 5.48 | 6.62 | 8.38 |
| Found: | 56.52 | 5.22 | 6.46 | 8.63 | b. In 6 ml. of toluene were dissolved 2.0 g. of 2,6-dimethyl-4-(3′-nitrophenyl)-1,4-dihydropyridine-3,5-dicarboxylic acid 3-β-chloroethyl ester 5-isopropyl ester and 1.4 g. of N-ethylbenzylamine and the solution was refluxed for 5 hours. After the reaction was over, the reaction mixture was mixed with 30 ml. of chloroform and 10 ml. of water and the organic layer thus formed was separated, dried over anhydrous magnesium sulfate, and distilled under reduced pressure to remove the solvent. The residue was subjected to a silica gel column chromatography (diameter 4 cm., height 25 cm.), the product was eluted using a mixture of benzene and acetone in 10 : 1 volume ratio, and then the effluents containing the aimed product were collected and concentrated under reduced pressure. The residue obtained was dissolved in ethanol and after acidifying the solution with an ethanol solution of hydrochloric acid, the solution was concentrated under reduced pressure. By recrystallizing the product from a chloroform-ether mixture there is obtained 1.1 g. of 2,6-dimethyl-4-(3′-nitrophenyl)-1,4-dinitropyridine-3,5-dicarboxylic acid 3-β-(N-benzyl-N-ethylamino)ethyl ester 5-isopropyl ester hydrochloride was obtained.

Melting point: 132°–135° C.

Elemental analysis for $C_{29}H_{36}N_3O_6Cl$:

|  | C(%) | H(%) | N(%) | Cl(%) |
|---|---|---|---|---|
| Calculated: | 62.41 | 6.50 | 7.53 | 6.35 |
| Found: | 62.30 | 6.38 | 7.49 | 6.41 |

EXAMPLE 13

A mixture of 5.26 g. of acetoacetic acid β-(N-methyl-N-p-methylbeznylamino)ethyl ester, 2.86 g. of β-aminocrotonic acid isopropyl ester, and 3.02 g. of m-nitrobenzaldehyde was stirred for 6 hours at 100° C. on an oil bath.

21

After the reaction was over, the reaction mixture was subjected to a silica gel column chromatography (diameter 4 cm., height 25 cm.), the product was, then, eluted therefrom with a mixture of chloroform and acetone in 20 : 1 volume ratio, and then the effluents containing the product were checked with a thin layer chromatography, collected and concentrated to provide 2,6-dimethyl-4-(3'-nitrophenyl)-1,4-dihydropyridine-3,5-dicarboxylic acid 3-isopropyl ester 5-$\beta$-(N-methyl-N-p-methylbenzylamino)ethyl ester.

The product was dissolved in acetone and after adjusting the solution thus prepared to pH 1–2 with an ethanol solution saturated with hydrogen chloride, the solution was concentrated. The residue formed was dissolved in a small amount of acetone and by adding petroleum ether to the solution, 4 g. of the powder of 2,6-dimethyl-4-(3'-nitrophenyl)-1,4-dihydropyridine-3,5-dicarboxylic acid 3-isopropyl ester 5-$\beta$-(N-methyl-N-p-methylbenzylamino)ethyl ester hydrochloride was obtained.

Elemental analysis for $C_{29}H_{36}N_3O_6Cl$:

|  | C(%) | H(%) | N(%) | Cl(%) |
|---|---|---|---|---|
| Calculated: | 62.41 | 6.50 | 7.53 | 6.35 |
| Found: | 62.61 | 6.69 | 7.23 | 6.35 |

EXAMPLE 14

A mixture of 5.0 g. of acetoacetic acid $\beta$-(N-methyl-N-p-methoxybenzylamino) ethyl ester, 2.4 g. of $\beta$-aminocrotonic acid ethyl ester, and 2.4 g. of m-nitrobenzaldehyde was heated to 85° C. for 5 hours. Then, by treating the reaction mixture thus obtained as in Example 13, 4.1 g. of 2,6-dimethyl-4-(3'-nitrophenyl)-1,4-dihydropyridine-3,5-dicarboxylic acid 3-ethyl ester 5-$\beta$-(N-methyl-N-p-methoxybenzylamino)ethyl ester was obtained.

The nuclear magnetic resonance spectra of this product agreed with its chemical structure.

Elemental analysis for $C_{28}H_{33}N_3O_7$:

|  | C(%) | H(%) | N(%) |
|---|---|---|---|
| Calculated: | 64.23 | 6.35 | 8.03 |
| Found: | 64.01 | 6.41 | 7.85 |

EXAMPLE 15

A mixture of 1.5 g. of m-nitrobenzaldehyde, 2.8 g. of acetoacetic acid $\beta$-(N-methyl-N-p-chlorobenzylamino)ethyl ester, 1.3 g. of $\beta$-aminocrotonic acid ethyl ester, and 5 ml. of ethanol was stirred for 3 hours at 95° C.

The solvent was distilled off under reduced pressure from the reaction mixture, the residue was subjected to a silica gel column chromatography, and the product was eluted with a benzene-acetone mixture in 10 : 1 volume ratio. The effluents containing the aimed product were collected and the solvent was distilled away. The residue formed was dissolved in ethanol and after acidifying the solution with a 1 N ethanolic hydrochloric acid solution, ethanol was distilled away under reduced pressure. The residue thus formed was dissolved in a small amount of acetone and after adding ether to the solution until turbid, the solution was allowed to stand at 0° C. to provide 2.8 g. of the light-yellow acicular crystals or 2,6-dimethyl-4-(3'-nitrophenyl)-1,4-dihydropyridine-3,5-dicarboxylic acid 3-ethyl ester 5-$\beta$-(N-methyl-N-p-chlorobenzylamino)ethyl ester hydrochloride.

Melting point: 135°–139° C. (decomposed)
Elemental analysis for $C_{27}H_{31}N_3O_6Cl_2$:

|  | C(%) | H(%) | N(%) | Cl(%) |
|---|---|---|---|---|
| Calculated: | 57.45 | 5.54 | 7.44 | 12.56 |
| Found: | 57.10 | 5.62 | 7.35 | 12.77 |

EXAMPLE 16

In 20 ml. of isopropyl alcohol were dissolved 7.0 g. of acetoacetic acid $\beta$-(N-methyl-N-p-methoxybenzylamino)ethyl ester, 2.0 g. of m-nitrobenzaldehyde, and 2.2 ml. of 28% ammonia water and the solution was stirred for 6 hours at 85° C. The reaction mixture was dissolved in ethyl acetate and then extracted once with an excess of dilute hydrochloric acid and three times with water. The extracts were combined and after basifying the mixture with a dilute aqueous solution of sodium hydroxide, the product was extracted with chloroform. The extract was dried over anhydrous magnesium sulfate and then chloroform was distilled off under reduced pressure. The residue was subjected to a silica gel column chromatography and the product was eluted for purification with ethyl acetate. The fractions of the aimed product were collected and concentrated. Then, after acidifying the residue with 1 N ethanolic hydrochloric acid solution, the solvent was distilled away under reduced pressure to provide 5.0 g. of the crystalline powder of 2,6-dimethyl-4-(3'-nitrophenyl)-1,4-dihydropyridine-3,5-dicarboxylic acid bis[$\beta$-(N-methyl-N-p-methoxyphenylamino)ethyl]-ester dihydrochloride.

Elemental analysis for $C_{37}H_{46}N_4O_8Cl_2$:

|  | C(%) | H(%) | N(%) | Cl(%) |
|---|---|---|---|---|
| Calculated: | 59.60 | 6.22 | 7.51 | 9.51 |
| Found: | 59.55 | 6.03 | 7.79 | 9.69 |

EXAMPLE 17

In 3 ml. of isopropyl alcohol were dissolved 1.6 g. of o-trifluoromethyl benzaldehyde, 1.6 g. of $\beta$-aminocrotonic acid $\beta$-(N-benzyl-N-ethylamino)ethyl ester, and 0.9 g. of acetoacetic acid propoxyethyl ester and then the solution was stirred for 14 hours at 85° C. The reaction mixture was concentrated, the residue was dissolved in a small amount of a chloroform-acetone mixture in 20 : 1 volume ratio, and then the solution was subjected to a silica gel column chromatography (diameter 3.5 cm., height 20 cm.). The product was eluted therefrom with a chloroform-acetone mixture in 20 : 1 volume ratio and the effluents containing the aimed product were checked with a thin layer chromatography, collected and concentrated to provide 0.6 g. of 4-(2-trifluoromethylphenyl)-2,6-dimethyl-1,4-dihydropyridine-3,5-dicarboxylic acid 3-$\beta$-(N-benzyl-N-ethylamino)ethyl ester 5-$\beta$-propoxyethyl ester.

Elemental analysis for $C_{32}H_{39}N_2O_5F_3$:

|  | C(%) | H(%) | N(%) |
|---|---|---|---|
| Calculated: | 65.23 | 6.68 | 4.76 |
| Found: | 65.37 | 6.89 | 4.82 |

EXAMPLE 18

In 3 ml. of isopropyl alcohol were dissolved 1.07 g. of acetoacetic acid β-(N-methyl-N-p-methylbenzylamino)ethyl ester, 0.466 g, of β-aminocrotonic acid methyl ester, and 0.705 g. of m-trifluoromethyl benzaldehyde and the solution was refluxed for 6 hours. The reaction mixture was concentrated, subjected to a silica gel column chromatography (diameter 4 cm, height 15 cm.), and then the effluents containing the aimed product obtained were collected and concentrated. The residue thus obtained was dissolved in acetone and after adjusting the solution to pH 1-2 with an ethanol solution saturated with hydrogen chloride, the solution was concentrated. Then, by crystallizing the residue formed with acetone, 0.8 g. of 2,6-dimethyl-4-(3'-trifluoromethylphenyl)-1,4-dihydropyridine-3,5-dicarboxylic acid 3-methyl ester 5-β-(N-methyl-N-p-methylbenzylamino)ethyl ester hydrochloride was obtained.

Elemental analysis for $C_{28}H_{32}N_2O_4F_3Cl$:

|  | C(%) | H(%) | N(%) | Cl(%) |
|---|---|---|---|---|
| Calculated: | 60.81 | 5.83 | 5.07 | 6.41 |
| Found: | 61.11 | 6.01 | 5.35 | 6.67 |

EXAMPLE 19

A mixture of 1 g. of acetylacetone, 0.75 ml. of concentrated ammonia water, 1.5 g. of m-nitrobenzaldehyde, 2.5 g. of acetoacetic acid β-(N-benzyl-N-methylamino)ethyl ester, and 5 ml. of ethanol was heated to 90° C. for 4 hours. After distilling off the solvent from the reaction mixture under reduced pressure, the residue was dissolved in 10 ml. of ethyl acetate and then the product was extracted with 2 N hydrochloric acid solution. The extract was neutralized with sodium carbonate and then the product was extracted with ethyl acetate. The solvent was distilled away from the extract under reduced pressure and the residue formed was dissolved in 3 ml. of ethanol. After acidifying the solution with 2 N ethanolic hydrogen chloride solution, ethyl acetate was added to the solution until turbid and then the solution was allowed to stand for 20 hours at 0° C. to provide 1.4 g. of the yellow acicular crystals of 5-acetyl-2,6-dimethyl-4-(3'-nitrophenyl)-1,4-dihydropyridine-3-carboxylic acid β-(N-benzyl-N-methylamino) ethyl ester hydrochloride.

Melting point: 154°–157° C. (decomposed)
Elemental analysis for $C_{26}H_{30}N_3O_5Cl$:

|  | C(%) | H(%) | N(%) | Cl(%) |
|---|---|---|---|---|
| Calculated: | 62.46 | 6.05 | 8.40 | 7.09 |
| Found: | 62.75 | 6.21 | 8.22 | 6.99 |

EXAMPLE 20

To 1 g. of acetylacetone were added 0.75 ml. of concentrated ammonia water and 5 ml. of ethanol and the mixture was stirred for 30 minutes at room temperature, whereby crystals were formed. To the product were added 1.5 g of m-nitrobenzaldehyde and 2.8 g. of acetoacetic acid β-(N-p-chlorobenzyl-N-methyl)ethyl ester and the mixture was heated for 4 hours to 95° C. The solvent was distilled away from the reaction mixture under reduced pressure and the residue was subjected to a silica gel column chromatograhy. Then, the fractions containing the product were eluted therefrom with a benzeneacetone mixture in 10 : 1 volume ratio, the elutes were collected and then the solvent was distilled off under reduced pressure. The residue was dissolved in ethanol and after acidifying the solution with 2N ethanolic hydrogen chloride solution, ethyl acetate was added to the solution until turbid. Then, the solution was allowed to stand for 3 days at 0° C to provide 1.2 g. of the yellow acidular crystals of 5-acetyl-2,6-dimethyl-4-(3'-nitrophenyl)-1,4-dihydropyridine-3-carboxylic acid β-(N-p-chloro-benzyl-N-methylamino) ethyl ester hydrochloride Melting point 145°–150° C. (decomposed)
Elemental Analysis for $C_{26}H_{29}N_3O_5Cl$:

|  | C(%) | H(%) | N(%) | Cl(%) |
|---|---|---|---|---|
| Calculated: | 58.43 | 5.47 | 7.86 | 13.27 |
| Found: | 58.65 | 5.59 | 7.68 | 13.10 |

EXAMPLE 21

In 15 ml. of isopropanol were dissolved 5.0g. of β-aminocrotonic acid N-benzyl-N-methylaminoethyl ester, 3.1g. of m-nitro-benzaldehyde, and 2.0g. of acetylacetone and then the solution was stirred for 4 hours at 85° C. The reaction mixture was dissolved in 40 ml. of ethyl acetate and then the product was extracted with an excess of dilue aqueous hydrochloric acid and then extracted three times each with 40 ml. of water. The aqueous extracts were combined, and then 10 g. of sodium chloride was dissolved in the extract. Then, the oily material thus formed was extracted four times each with 50 ml. of chloroform. The chloroform extracts were combined, dried over anhydrous magnesium sulfate, and then chloroform was distilled away under reduced pressure. The residue was dissolved in acetone and then ethyl acetate was added to the solution to provide 5.0 g. of the yellow acidular crystals of 5-acetyl-2,6-dimethyl-4-(3'-nitrophenyl)-1,4-dihydropyridine-3-carboxylic acid β-(N-benzyl-N-methylamino) ethyl ester hydrochloride.

Melting point: 154°–157° C. (decomposed).

EXAMPLE 22

In 20 ml. of isopropyl alcohol were dissoled 2.9 g. of 2-amino-2-penten-4-one, 4.41 g of m-nitrobenzaldehyde, and 7.7 g. of acetoacetic acid β-(N-benzyl-N-methylamino)ethyl ester and then the solution was refluxed for 6 hours. To the reaction mixture was added 70 ml. of ethyl acetate and after adjusting the solution to pH 1-2 with 2N hydrochloric acid, the aqueous layer thus formed was separated. The ethyl acetate layer formed was extracted twice with water. The aqueous layers were combined and after saturating the solution with sodium chloride, the product was extracted twice each with chloroform. The chloroform extracts were combined and dried over anhydrous magnesium sulfate and concentrated. When a small amount of ethanol was added to the concentrate, crystals were formed, which were recovered by filtration and recrystallized from ethanol to provide 7 g. of 5-acetyl-2,6-dimethyl-4-(3'-nitrophenyl)-1,4-dihydropyidine-3-carboxylic acid β-(N-benzyl-N-methylamino)ethyl ester hydrochloride.

Melting point: 147°–152° C. (decomposed).
Elemental analysis for $C_{26}H_{30}N_3O_5Cl \cdot C_2H_5OH$:

|  | C(%) | H(%) | N(%) | Cl(%) |
|---|---|---|---|---|
| Calculated: | 61.77 | 6.62 | 7.67 | 6.79 |
| Found: | 61.59 | 6.65 | 7.70 | 6.49 |

EXAMPLE 23

In 3 ml. of isopropanol were dissolved 1.18 g. of acetoacetic acid N-benzyl-N-methylaminoethyl ester, 0.48 g. of 2-amino-2-penten-4-one, and 0.83 g. of m-trifluoromethyl benzaldehyde and then the solution was refluxed for 6 hours.

The reaction mixture was concentrated and the residue was subjected to a silica gel column chromatography (diameter 4 cm. height 15 cm.). The product was eluted with a chloroform-acetone mixture in 20 : 1 volume ratio, the effluents containing the product were checked with a thin layer chromatography, collected and then concentrated. The residue formed was dissolved in acetone and after adjusting the solution to pH 1-2 with an ethanol solution saturated with hydrogen chloride, the solution was concentrated. The crystals formed were recrystallized from acetone to provide 1.3 g of 5-acetyl-2,6-dimethyl-4-(3'-trifluoromethylphenyl)-1,4-dihydropyridine-3-carboxylic acid β-(N-benzyl-N-methylamino)ethyl ester hydrochloride.

Melting point: 168°–169° C. (decomposed)
Elemental analysis for $C_{27}H_{30}N_2O_3F_3Cl$:

|  | C(%) | H(%) | N(%) | Cl(%) |
|---|---|---|---|---|
| Calculated: | 62.01 | 5.78 | 5.36 | 6.78 |
| Found: | 62.30 | 5.90 | 5.33 | 6.95 |

EXAMPLE 24

A mixture of 1.0 g. of o-trifluoromethyl benzaldehyde, 1.6 g. of acetoacetic acid β-(N-benzyl-N-methylamino)ethyl ester, and 700 mg. of β-aminocrotonic acid methyl ester was stirred for 6 hours at 110°–120° C. The reaction mixture was dissolved in a small amount of a chloroform-acetone mixture in 20 : 1 volume ratio and then the solution was subjected to a silica gel column chromatograhy (diameter 3.5 cm., height 20 cm.). The product was eluted with a chloroform-acetone solution in 20 : 1 colume ratio and then the effluents containing the aimed product were checked with a thin layer chromatography collected and then concentrated. The residue was dissolved in a small amount of acetone and after acidifying the solution with an ethanol solution saturated with hydrogen chloride, the solution was concentrated. The residue obtained was treated with acetone-ether mixture and crystallized to provide 0.7 g. of 2,6-dimethyl-4-(o-trifluoromethyl-phenyl)-1,4-dihydropyridine-3,5-dicarboxylic acid 3-β-(N-benzyl-N-methylamino)ethyl ester 5-methyl ester hydrochloride.

Melting point: 182°–192° C.
Elemental analysis for $C_{27}H_{30}N_2O_4F_3Cl$:

|  | C(%) | H(%) | N(%) | Cl(%) |
|---|---|---|---|---|
| Calculated: | 60.17 | 5.61 | 5.20 | 6.58 |
| Found: | 59.93 | 5.86 | 5.48 | 6.90 |

EXAMPLE 25

In 3 ml. of isopropyl alcohol were dissolved 1.18 g. of acetoacetic acid β-(N-benzyl-N-methylamine)ethyl ester, 0.55 g. of β-aminocrotonic acid methyl ester, and 0.3 g. of m-trifluoromethyl benzaldehyde and the solution was refluxed for 6 hours. The reaction mixture was concentrated and the residue was subjected to a silica gel column chromatography (diameter 4 cm., height 15 cm.). The product was then eluted with a chloroform-acetone mixture in 20 : 1 volume ratio and the effluents containing the product were checked with a thin layer chromatography, collected and concentrated. The residue formed was dissolved in acetone and after adjusting the solution to pH 1–2 with an ethanol solution saturated with hydrogen chloride, the solution was concentrated. By crystallizing the residue thus formed using ethyl acetate, 1.3 g. of 2,6-dimethyl-4-(m-trifluoromethylphenyl)-1,4-dihydropyridine-3,5-dicarboxylic acid 3-β-(N-benzyl-N-methylamino)ethyl ester 5-methyl ester hydrochloride was obtained.

Melting point: 142°–152° C. (decomposed).
Elemental analysis for $C_{27}H_{30}N_2O_4F_3Cl$:

|  | C(%) | H(%) | N(%) | Cl(%) |
|---|---|---|---|---|
| Calculated: | 60.17 | 5.61 | 5.20 | 6.58 |
| Found: | 60.47 | 5.63 | 5.49 | 6.71 |

EXAMPLE 26

In 3 ml. of isopropyl alcohol were dissolved 1.07 g. of acetoacetic acid β-(N-benzyl-N-methylamino)propyl ester, 0.52 g. of β-aminocrotonic acid ethyl ester, and 0.71 g. of m-trifluoromethyl benzaldehyde and the solution was refluxed for 6 hours.

Then, as in Example 25, the reaction mixture was subjected to a silica gel column chromatography and the effluents containing the aimed product were collected and concentrated to provide 0.9 g. of 2,6-dimethyl-4-(m-trifluoromethylphenyl)-1,4-dihydropyridine-3,5-dicarboxylic acid 3-β-(N-benzyl-N-methylamino)-propyl ester 5-ethyl ester.

Elemental analysis for $C_{29}H_{33}N_2O_4F_3$:

|  | C(%) | H(%) | N(%) |
|---|---|---|---|
| Calculated: | 65.65 | 6.27 | 5.28 |
| Found: | 65.45 | 6.40 | 5.40 |

EXAMPLE 27

A mixture of 1.5 g of 2-(3-nitrobenzdilidene)acetoacetic acid β-(N-benzyl-N-methylamino)ethyl ester, 0.452 g. of β-aminocrotonic acid methyl ester, and 7 ml. of isopropyl alcohol was refluxed for 6 hours with stirring. After cooling, the reaction mixture was mixed with 30 ml. of chloroform and then with 10 ml. of 2 N aqueous hydrochloric acid solution. The mixture was shaken in a separating funnel, washed twice with water, and the chloroform layer thus formed was separated. The chlorofrom layer thus obtained was concentrated and after adding 7 ml. of ethyl acetate to the residue formed, the mixture was stirred overnight, whereby 1.4 g. of crystals were obtained. The crystals were dissolved in methanol and after distilling away the solvent from the solution, the residue was recrystallized from acetone to provide 0.98 g. of 2,6-dimethyl-4-(3'-nitrophenyl)-1,4-dihydropyrydine-3,5-dicarboxylic acid 3-methyl ester 3-β-(N-benzyl-N-methylamino)ethyl ester 5-methyl ester hydrochloride.

Elemental analysis for $C_{26}H_{30}N_3O_6Cl$:

|  | C(%) | H(%) | N(%) | Cl(%) |
|---|---|---|---|---|
| Calculated: | 60.52 | 5.86 | 8.14 | 6.87 |
| Found: | 60.76 | 5.72 | 8.04 | 7.00 |

EXAMPLE 28

A mixture of 1.1 g. of 2-(3'-nitrobenzylidene)acetoacetic acid β-(N-benzyl-N-methylamino)ethyl ester, 0.34 g. of acetoacetic acid methyl ester, 5 ml. of ethanol, and 0.35 ml. of ammonia water was refluxed for 5 hours with stirring. After distilling away the solvent, the reaction mixture was treated by the same way as in Example 27 to provide 0.33 g of 2,6-dimethyl-4-(3'-nitrophenyl)-1,4-dihydropyridine-3,5-dicarboxylic acid 5-β-(N-benzyl-N-methylamino)-ethyl ester 5-methyl ester hydrochloride.

The infrared absorption spectra of this product coincided with the infrared absorption spectra of the product obtained in Example 27.

EXAMPLE 29

A mixture of 2.49 g. of 2-(3'-nitrobenzylidene)acetoacetic acid methyl ester, 2.48 g. of β-aminocrotonic acid β-(N-benzyl-N-methylamino)ethyl ester, and 8 ml. of isopropyl alcohol was refluxed for 6 hours with stirring. After cooling, the reaction mixture was mixed with 100 ml. of chloroform for dissolving the product therein and washed with 2N aqueous hydrochloric acid solution adjusting the aqueous layer formed to pH 1-2.

Then, the chloroform solution was washed twice with water and the chloroform layer formed was dried over anhydrous sodium sulfate and concentrated. The residue formed was mixed with 20 ml. of ethyl acetate, whereby 3.3 g. of crystals were obtained. The crystals were dissolved in methanol and then the solvent was distilled away, to provide a sticky material. By recrystallizing the material from acetone, 2 g. of 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride was obtained.

The infrared absorption spectra of the product coincided with the infrared absorption spectra of the product obtained in Example 27.

EXAMPLE 30

A mixture of 2.49 g. of 2-(3'-nitrobenzylidene)acetoacetic acid methyl ester, 2.49 g. of acetoacetic acid β-(N-benzyl-N-methylamino)ethyl ester, 1.18 ml. of ammonia water, and 10 ml. of ethanol was refluxed for 6 hours with stirring. Then, the reaction mixture was concentrated, the residue formed was subjected to a silica gel column chromatography, and the aimed portions were eluted with a chloroform-acetone mixture in 10 : 1 volume ratio. The recovered portions were dissolved in chloroform and washed with 2 N hydrochloric acid adjusting the aqueous layer formed to pH 1-2.

Then, the solution was washed twice with water and the coloroform layer formed was separated, dried over anhydrous sodium sulfate, and concentrated. When ethyl acetate was added to the residue formed, 1.1 g. of crystal formed. The crystals were recovered and dissolved in methanol. Then, when the solvent was distilled away from the solution, a sticky material was obtained. By crystallizing the material from acetone, 0.7 g. of 2,6-dimethyl-4-(3'-nitrophenyl)-1,4-dihydropyridine-3,5-dicarboxylic acid 3β-(N-benzyl-N-methylamino)ethyl ester 5-methyl ester hydrochloride was obtained.

The infrared absorption spectra of this product agreed with the infrared absorption spectra of the compound obtained in Example 27.

EXAMPLE 31

In 7 ml of pyridine were dissolved 675 mg of methylamine hydrochloride, 2.49 g of acetoacetic acid β-(N-benzyl-N-methylamino)ethyl ester, 1.17 g of acetoacetic acid methyl ester and 1.51 g of m-nitrobenzaldehyde and the mixture was heated 90° C for 3 hours. The reaction mixture was cooled and 30 ml of chloroform was added and was washed with 10 ml of water, 10 ml of 2% acetic acid, 10 ml of 3% sodium hydroxide and 10 ml of water successively. The chloroform layer was dried over anhydrous magnesium sulfate and concentrated.

The residue obtained was dissolved in a small amount of a mixture of benzene and acetone, volume ratio is 8:1, and subjected to silica gel column chromatography (diameter 4 cm, height 25 cm). The effluent was checked by thin layer chromatography and the effluents containing the aimed product were collected and the combined effluents were condensed. The resulted oily material was dissolved in a small amount of acetone and acidified by ethanolic hydrogen chloride, whereby 1.1 g of 1,2,6-trimethyl-4-(3'-nitrophenyl)-1,4-dihydropyridine-3,5-dicarboxylic acid 3-β-(N-benzyl-N-methylamino)ethyl ester 5-methyl ester hydrochloride was obtained.

Elemental analysis for $C_{27}H_{32}N_3O_6Cl$

|  | C(%) | H(%) | N(%) | Cl(%) |
|---|---|---|---|---|
| Calculated: | 61.19 | 6.08 | 7.93 | 6.69 |
| Found: | 61.03 | 6.12 | 7.72 | 6.81 |

EXAMPLE 32

In 7 ml of pyridine were dissolved 675 mg of methylamine hydrochloride, 2.48 g of m-nitrobenzylidene acetoacetic acid methyl ester and 2.49 g of acetoacetic acid β-(N-benzyl-N-methylamino)-ethyl ester and the mixture was heated 90° C for 2 hours. The reaction mixture was treated similarly to example 31 and 1.2 g of 1,2,6-trimethyl-4-(3'-nitrophenyl)-1,4-dihydropyridine-3,5-dicarboxylic acid 3- β-(N-benzyl-N-methylamino)ethyl ester 5-methyl ester hydrochloride. The infrared spectra of the product was identical to those of the example 31.

EXAMPLE 33

A sterile aqueous solution for injection, containing in 1 ml 0.1 mg of 2,6-dimethyl-4-(3'-nitrophenyl)-1,4-dihydropyridine-3,5-dicarboxylic acid 3- β-(N-benzyl-N-methylamino)ethyl ester 5-methyl ester hydrochloride is prepared from the following formula.

| | |
|---|---|
| 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride | 10 mg |
| sodium chloride | 900 mg |
| water for injection q.s. | 100 ml |

Above ester compound was dissolved in about 80 ml of water, then the resultant solution was filled up to 100 ml by the addition of water and sterilized by filtration. The sterile solution is filled in 100 light intercepting vials and the vials sealed.

EXAMPLE 34

A tablet containing in 1 tablet 10 mg of 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride is prepared from the following formula.

| | |
|---|---|
| 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride | 10 g |
| lactose | 80 g |
| starch | 29 g |
| magnesium stearate | 1 g |

EXAMPLE 35

A sterile aqueous solution for injection, containing in 1 ml 1.0 mg of 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride is prepared from the following formula.

| | |
|---|---|
| 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride | 100 mg |
| Glucose | 5000 mg |
| water for injection q.s. | 100 ml |

Above ester compound was dissolved in about 80 ml of water, then the resultant solution was filled up to 100 ml by the addition of water and sterilized by filtration. The sterile solution is filled in 100 light intercepting vials and the vials sealed.

EXAMPLE 36

A tablet containing in 1 tablet 10 mg of 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride is prepared from the following formula.

| | |
|---|---|
| 2,6-dimethyl-4-(3'-nitrophenyl)-1,4-dihydropyridine-3,5-dicarboxylic acid 3-β-(N-benzyl-N-methylamino)ethyl ester 5-methyl ester hydrochloride | 10 g |
| lactose | 80 g |
| starch | 29 g |
| magnesium stearate | 1 g |

EXAMPLE 37

In 7 ml of isopropanol were dissolved 3 g of o-nitrobenzaldehyde, 4.98 g of acetoacetic acid β-(N-benzyl-N-methylamino) ethyl ester and 2.3 g of β-crotonic acid methyl ester, and then the solution thus prepared was refluxed for 5 hours.

After the reaction was complete, the reaction mixture was concentrated and the residue thus obtained was dissolved in a small amount of chloroform-aceton mixture of 10 : 1 by volume ratio and the solution obtained was subjected to a silica gel column chromatography. The product was eluted with a chloroform-aceton mixture of 10 : 1 by volume ratio. The effluent was checked with a thin layer chromatography and the effluent containing the aimed product was collected and was concentrated. The residue formed was dissolved in aceton and after adjusting the solution to PH 1-2 with an ethanol solution saturated with hydrogen chloride, the solution was concentrated.

The residue was dissolved in a small amount of aceton and to the solution formed, ether was added to provide 3.2 g of the solid 2,6-dimethyl-4-(2'-nitrophenyl)-1,4-dihydropyridine-3.5-dicarboxilic acid 3-methyl ester 5-β-(N-benzyl-N-methylamino) ethyl ester hydrochloride.

Melting point: 181°–183° C.

Elemental analysis for $C_{26}H_{30}N_3O_6Cl$:

| | C(%) | H(%) | N(%) | Cl(%) |
|---|---|---|---|---|
| Calculated | 60.52 | 5.86 | 8.14 | 6.87 |
| Found | 60.22 | 5.87 | 7.90 | 7.12 |

Above ester compound was finely pulverized and mixed with lactose and starch. The mixture was granulated by a conventional manner. Magnesium stearate was added to the granula and compressed to 1000 tablets each weighing 0.12 g.

What is claimed is:

1. A compound of the formula

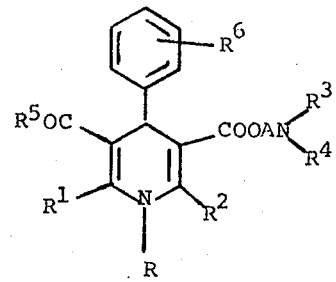

wherein R represents hydrogen or lower alkyl; $R^1$ and $R^2$ each represents methyl; $R^3$ represents phenyl, benzyl, halobenzyl, lower alkoxy-benzyl; $R^4$ represents hydrogen, methyl or ethyl; A represents lower alkylene; $R^5$ represents methyl, or lower alkoxy, or lower alkoxy substituted with lower alkoxy, or

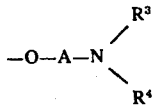

in which $R^3$ and $R^4$ have the same meaning as above; and $R^6$ represents nitro or trifluoromethyl.

2. The 1,4-dihydropyridine compound as claimed in claim 1 wherein said R is hydrogen, said $R^1$ and $R^2$ each represents methyl; said $R^3$ represents benzyl; said $R^4$ represents methyl or ethyl; said $R^5$ represents lower alkoxy; and said $R^6$ represents nitro.

3. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-benzyl-N-methylamino ethyl ester 5-methyl ester.

4. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-benzyl-N-methylamino) ethyl ester 5-ethyl ester.

5. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-benzyl-N-methylamino) ethyl ester 5-isopropyl ester.

6. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-benzyl-N-ethylamino) ethyl ester 5-isopropyl ester.

7. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-benzyl-N-methylamino) propyl ester 5-isopropyl ester.

8. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-p-methoxybenzyl-N-methylamino) ethyl ester 5-ethyl ester.

9. The 1,4-dihydropyridine compound as claimed in claim 1 which is 2,6-dimethyl-4-(3'-nitrophenyl)-1,4-dihydropyridine-3,5-dicarboxylic acid 3-$\beta$-(N-p-chlorobenzyl-N-methylamino) ethyl ester 5-ethyl ester.

* * * * *

UNITED STATES PATENT OFFICE
CERTIFICATE OF CORRECTION

Patent No. 3,985,758　　　　　Dated October 12, 1976

Inventor(s) Masuo Murakami, et al　　　　Page 1 of 4

It is certified that error appears in the above-identified patent and that said Letters Patent are hereby corrected as shown below:

In the Title Page, please insert the following Japanese patent applications upon which priority has also been based:

--No. 54939/1973 - May 17, 1973

No. 134069/1973 - November 29, 1973--

Column 1, line 58:　Change "20" to --$\underline{20}$--.

Column 1, line 61:　Change "71" to --$\underline{71}$--.

Column 2, line 23:　Change "(4-nitro..." to --(4-(nitro...--.

Column 2, line 31:　Change "58" to --$\underline{58}$--.

Column 3, line 22:　Change "re" to --are--.

Column 3, line 35:　Change "benzaldenyde" to --benzaldehyde--.

Column 4, line 9:　Delete "XVI".

Column 4, line 14:　Change "formual" to --formula--.

Column 6, line 60:　Delete "R".

Column 6, line 61:　Change the period after "above" to a comma.

UNITED STATES PATENT OFFICE
CERTIFICATE OF CORRECTION

Patent No. 3,985,758　　　　　　　　Dated　October 12, 1976

Inventor(s)　Masuo Murakami, et al

It is certified that error appears in the above-identified patent and that said Letters Patent are hereby corrected as shown below:

Column 7, line 45: Change "alkoxyl" to --alkoxy-- (both occurrences).

Column 8, line 25: Change "3-$\beta$-" to -- 3-$\gamma$- --.

Column 8, line 26: Change "5-ester isopropyl ester" to --ester 5-isopropyl ester--.

Column 8, lines 34, 37 and 48: Change "3-Acetyl" to --5-Acetyl--.

Column 8, lines 35, 38, 46 and 49: Change "5-carboxylic" to -- 3-carboxylic --.

Column 8, line 41: After "bis" change "]" to --[--.

Column 8, line 45: Change "3-pro-" to -- 5-pro --.

Column 8, line 47: Before "methyl" insert a hyphen.

Column 8, line 57: After "5-(2-propoxy)" insert a hyphen.

Column 8, line 61: Change "anesthethized" to --anesthetized--.

UNITED STATES PATENT OFFICE
CERTIFICATE OF CORRECTION

Patent No. 3,985,758    Dated  October 12, 1976

Inventor(s)  Masuo Murakami, et al        Page 3 of 4

It is certified that error appears in the above-identified patent and that said Letters Patent are hereby corrected as shown below:

Column 9, line 61 and Column 10, line 40:  Change "anesthethized" to --anesthetized--.

Column 18, line 19:  Change "eithyl" to --ethyl--.

Column 18, line 26:  Change "methylaminethyl" to --methylaminoethyl--.

Column 19, line 59:  After "ester" insert --3--.

Column 19, line 59 and Column 27, line 20:  Delete "3-methyl ester".

Column 20, line 45:  Change "ethanol" to --ethanolic--.

Column 20, line 65:  Change "methyl-beznylamino" to --methyl-benzylamino--.

Column 25, line 2:  Delete "each".

Column 27, line 41:  Change "5-$\beta$ -(N-benzyl-N-methylamino)" to -- 3-$\beta$ -(N-benzyl-N-methylamino) --.

UNITED STATES PATENT OFFICE
CERTIFICATE OF CORRECTION

Patent No. 3,985,758　　　　　Dated October 12, 1976

Inventor(s) Masuo Murakami et al.

It is certified that error appears in the above-identified patent and that said Letters Patent are hereby corrected as shown below:

Column 30, lines 27, 31 and 35: change "aceton" to -- acetone --.

Signed and Sealed this

Seventeenth Day of May 1977

[SEAL]

Attest:

RUTH C. MASON  
Attesting Officer

C. MARSHALL DANN  
Commissioner of Patents and Trademarks

UNITED STATES PATENT OFFICE
CERTIFICATE OF CORRECTION

Patent No. 3,985,758                    Dated October 10, 1976

Inventor(s) Masuo Murakami et al.

It is certified that error appears in the above-identified patent and that said Letters Patent are hereby corrected as shown below:

Column 7, line 17: change "ounce" to --single dose--.

Columns 9 & 10, the structural formula before the first Table:

Change:

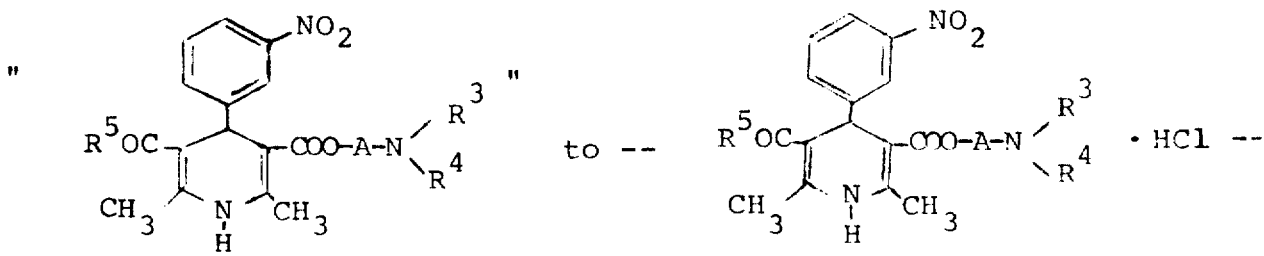

Columns 9 & 10, first table, last line, change: "Nifedipine" to --Nifedipine base--.

UNITED STATES PATENT OFFICE
CERTIFICATE OF CORRECTION

Patent No. 3,985,758　　　　　　　　　Dated October 10, 1976

Inventor(s) Masuo Murakami et al.

It is certified that error appears in the above-identified patent and that said Letters Patent are hereby corrected as shown below:

Column 15, line 31: Change "nitrodiphenyl" to --nitrophenyl--.

Column 15, line 34: Change "acetone" to --acetone-ether--.

Column 15, line 37: Change "$C_6$" to --$O_6$--.

Column 20, line 49: Change "dinitropyridine" to --dihydropyridine--.

Signed and Sealed this

Twentieth Day of June 1978

[SEAL]

Attest:

RUTH C. MASON　　　　　　　　　DONALD W. BANNER
Attesting Officer　　　　　　　Commissioner of Patents and Trademarks

UNITED STATES PATENT AND TRADEMARK OFFICE

CERTIFICATE EXTENDING PATENT TERM
UNDER 35 U.S.C. 156

Patent No.    : 3,985,758

Dated         : October 12, 1976

Inventor(s)   : MASUO MURAKAMI ET AL

Patent Owner  : YAMANOUCHI PHARMACEUTICAL CO., LTD.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 11th day of December 1989.

Jeffrey M. Samuels
Acting Commissioner of
    Patents and Trademarks